(12) United States Patent
Mason et al.

(10) Patent No.: US 12,128,206 B2
(45) Date of Patent: *Oct. 29, 2024

(54) ANTIMICROBIAL NEEDLELESS CONNECTOR OR CATHETER

(71) Applicant: CareFusion 303, Inc., San Diego, CA (US)

(72) Inventors: Eugene Mason, La Habra Heights, CA (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 172 days.

This patent is subject to a terminal disclaimer.

(21) Appl. No.: 17/845,417

(22) Filed: Jun. 21, 2022

(65) Prior Publication Data

US 2022/0313975 A1 Oct. 6, 2022

Related U.S. Application Data

(63) Continuation of application No. 16/601,509, filed on Oct. 14, 2019, now Pat. No. 11,389,635.

(Continued)

(51) Int. Cl.
*A61M 39/16* (2006.01)
*A61M 39/10* (2006.01)

(52) U.S. Cl.
CPC ..... *A61M 39/16* (2013.01); *A61M 2039/1044* (2013.01); *A61M 2039/167* (2013.01);

(Continued)

(58) Field of Classification Search
CPC ............ A61M 39/16; A61M 2039/167; A61M 2205/0205; A61M 2205/0233; A61M 39/10; A61M 39/162
See application file for complete search history.

(56) References Cited

U.S. PATENT DOCUMENTS 5,322,520 A * 6/1994 Milder .................. A61N 1/306
604/20
2003/0209681 A1 11/2003 Leinsing et al.
(Continued)

FOREIGN PATENT DOCUMENTS

| CN | 1658923 A | 8/2005 |
|---|---|---|
| JP | H08506027 A | 7/1996 |

(Continued)

OTHER PUBLICATIONS

Chinese Office Action for Application No. 201980081512.6, dated Jul. 26, 2022, 20 pages including English translation.

(Continued)

*Primary Examiner* — Bradley J Osinski
(74) *Attorney, Agent, or Firm* — Morgan, Lewis & Bockius LLP

(57) ABSTRACT

A disclosed antimicrobial medical device includes a fluid transfer device configured to couple between a patient and a fluid reservoir, a fluid pathway extending through the fluid transfer device, a first electrode coupled to the fluid transfer device, and a second electrode coupled to the fluid transfer device and spaced apart from the first electrode. The first electrode includes a first conductive material and the second electrode includes a second conductive material different from the first conductive material. The second electrode is configured to form a galvanic cell with the first electrode.

14 Claims, 5 Drawing Sheets

Related U.S. Application Data

(60) Provisional application No. 62/745,918, filed on Oct. 15, 2018.

(52) U.S. Cl.
CPC ............... *A61M 2205/0205* (2013.01); *A61M 2205/0233* (2013.01); *A61M 2205/583* (2013.01)

(56) References Cited

U.S. PATENT DOCUMENTS

| | | |
|---|---|---|
| 2008/0125838 A1 | 5/2008 | Francis |
| 2012/0078203 A1 | 3/2012 | Gaube et al. |
| 2014/0058336 A1* | 2/2014 | Burkholz ............... A61M 39/26 604/256 |
| 2014/0107740 A1* | 4/2014 | Crisp .................... A61N 1/205 607/115 |
| 2017/0136210 A1 | 5/2017 | Robertson et al. |

FOREIGN PATENT DOCUMENTS

| | | |
|---|---|---|
| JP | 2005511144 A | 4/2005 |
| JP | 2005524497 A | 8/2005 |
| WO | WO-9411058 A1 | 5/1994 |
| WO | WO-9738648 A1 | 10/1997 |
| WO | WO-03047636 A2 | 6/2003 |
| WO | WO-03095017 A1 | 11/2003 |
| WO | WO-2012162259 A2 | 11/2012 |

OTHER PUBLICATIONS

International Search Report and Written Opinion for Application No. PCT/US2019/056128, dated Feb. 6, 2020, 12 pages.
Chinese Office Action for Application No. 201980081512.6, dated Feb. 13, 2023, 15 pages including English translation.
Chinese Office Action for Application No. 201980081512.6, dated May 24, 2023, 13 pages including translation.
Japanese Office Action for Application No. 2021-545275, dated Jul. 21, 2023, 6 pages including translation.
Australian Office Action for Application No. 2019360184, dated Jun. 4, 2024, 3 pages.

* cited by examiner

ANTIMICROBIAL NEEDLELESS CONNECTOR OR CATHETER

CROSS REFERENCE

This application is a continuation of U.S. patent application Ser. No. 16/601,509, filed on Oct. 14, 2019, and entitled ANTIMICROBIAL NEEDLELESS CONNECTOR OR CATHETER, and claims priority from Provisional U.S. Patent Application Ser. No. 62/745,918 filed on Oct. 15, 2018, and entitled ANTIMICROBIAL NEEDLELESS CONNECTOR OR CATHETER.

FIELD OF THE INVENTION

The present disclosure generally relates to antimicrobial medical devices, and in particular, to antimicrobial medical devices with a galvanic cell.

BACKGROUND

Modern medical treatment often requires medical professionals to introduce fluids into a patient or withdraw fluids from a patient. For example, a patient may need treatment that requires a medical professional to withdraw urine or blood from the urethra or a vein, respectively. Conversely, the medical professional may need to introduce drugs or nutrients into the patient's vein (i.e., intravenously). To create a path for the flow of fluid into or from the patient, some methods involve use of a catheter where one end of the catheter is inserted into the patient. The other end of the catheter connects to a fluid reservoir, such as an intravenous (IV) bag or drainage bag connected through an IV line or other tubing. A needleless access connector may be coupled between the catheter and fluid reservoir to allow a medical practitioner to remove or add devices (e.g., IV bags) to the catheter without the use of a needle. However, fluid transfer devices can present a risk of infection a patient as the prolonged exposure leads to growth of bacteria or other microorganisms that can be transferred to the patient.

SUMMARY

The disclosed subject matter relates to antimicrobial medical devices. In certain embodiments, an antimicrobial medical device is disclosed that comprises a fluid transfer device configured to couple between a patient and a fluid reservoir; a fluid pathway extending through the fluid transfer device; at least one first electrode coupled to the fluid transfer device, the at least one first electrode comprising a first conductive material; and at least one second electrode coupled to the fluid transfer device and spaced apart from the at least one first electrode, the at least one second electrode comprising a second conductive material different from the first conductive material and being configured to form at least one galvanic cell with the at least one first electrode.

In certain embodiments, an antimicrobial needleless connector is disclosed that comprises a housing having an internal cavity and configured to couple between a patient and a fluid reservoir; a fluid pathway extending through the housing; a valve disposed within the internal cavity and configured to open and close the fluid pathway; at least one first electrode coupled the housing, the valve, or a combination thereof, the at least one first electrode comprising a first conductive material; and at least one second electrode coupled to the housing, the valve, or a combination thereof, the at least one second electrode being spaced apart from the at least one first electrode, the at least one second electrode comprising a second conductive material different from the first conductive material and being configured to form at least one galvanic cell with the at least one first electrode.

In certain embodiments, an antimicrobial catheter is disclosed that comprises a tubular member configured to couple between a patient and a fluid reservoir; a lumen extending through the tubular member and providing a fluid pathway to transfer fluid; at least one first electrode disposed around the fluid pathway, the at least one first electrode comprising a first conductive material; and at least one second electrode disposed around the fluid pathway and spaced apart from the at least one first electrode, the at least one second electrode comprising a second conductive material different from the first conductive material and being configured to form at least one galvanic cell with the at least one first electrode.

BRIEF DESCRIPTION OF THE DRAWINGS

FIG. 1A is a three-dimensional view showing components of the needless access connector in unassembled form. FIGS. 1B and 1C are cut-away views of the assembled needless access connector showing closed and open states, respectively.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

Antimicrobial medical devices and treatment methods, and more particularly, an electroceutical needless connector, catheter, or other electroceutical fluid transfer device may employ electrodes capable of forming a galvanic cell to combat the growth of bacteria. A galvanic cell (also referred to as a "voltaic" cell) is a type of electrochemical cell that can generate current from spontaneous reduction-oxidation reactions (also referred to as "redox") occurring within the cell. A galvanic cell includes two different electrodes spaced apart from one another and connected or connectable by an electrolytic or electrically conducting solution. For example, a galvanic cell may have two complementary electrodes made of zinc (Zn) and silver (Ag), respectively, that cause redox reactions when contacted and connected with an electrolytic solution. In this example, the Zn electrode provides the anode where oxidation occurs and the Ag electrode provides the cathode where the reduction reaction occurs. A variety of other conductive materials or metals may be suitable for the electrodes, provided that they are dissimilar and capable of forming a galvanic electric field. These electrodes may be implemented as dots, bands, or larger areas in close proximity on fluid transfer devices to create a galvanic electric field in the presence of body tissue or fluid.

Figure 1A:
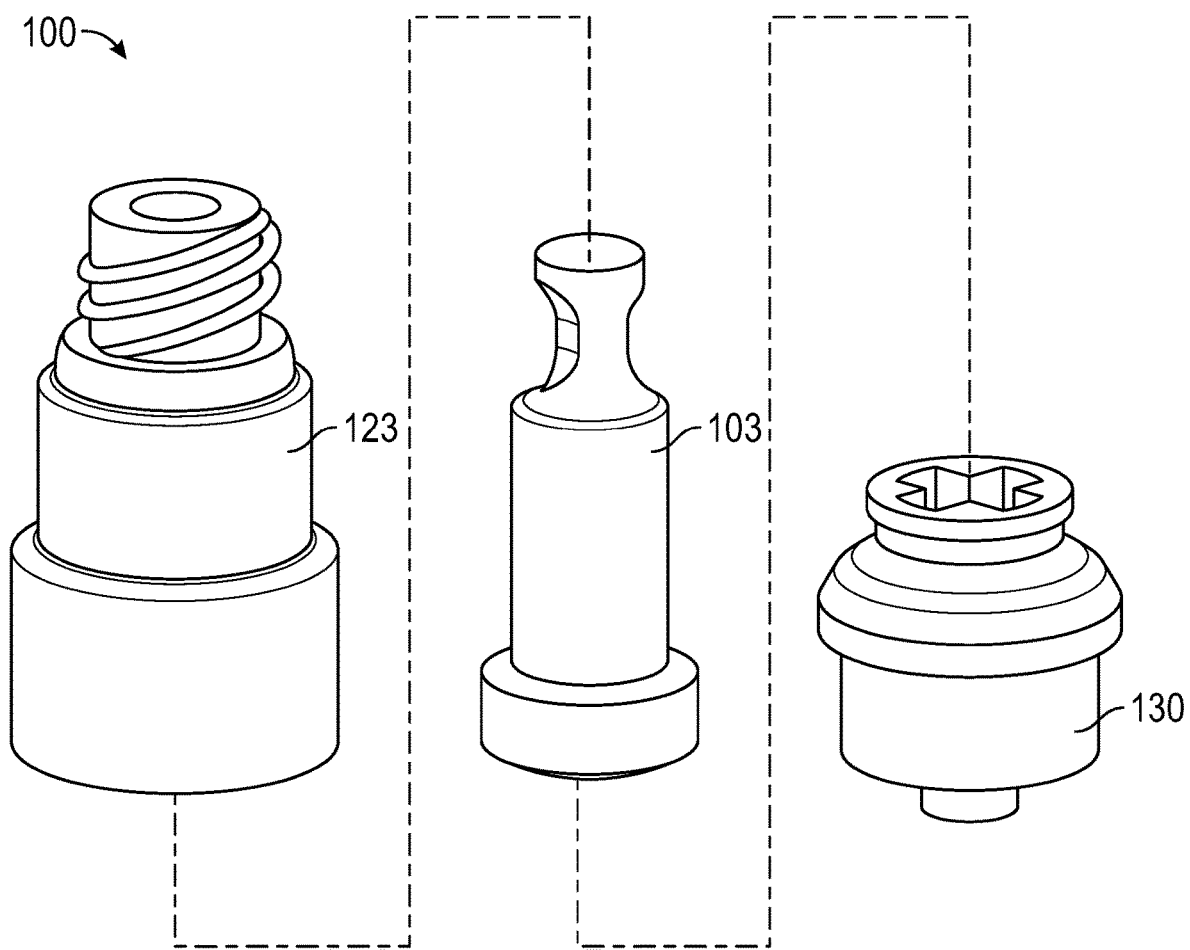
FIGS. 1A-1C are views of an example needless access connector.
Figure 1B:
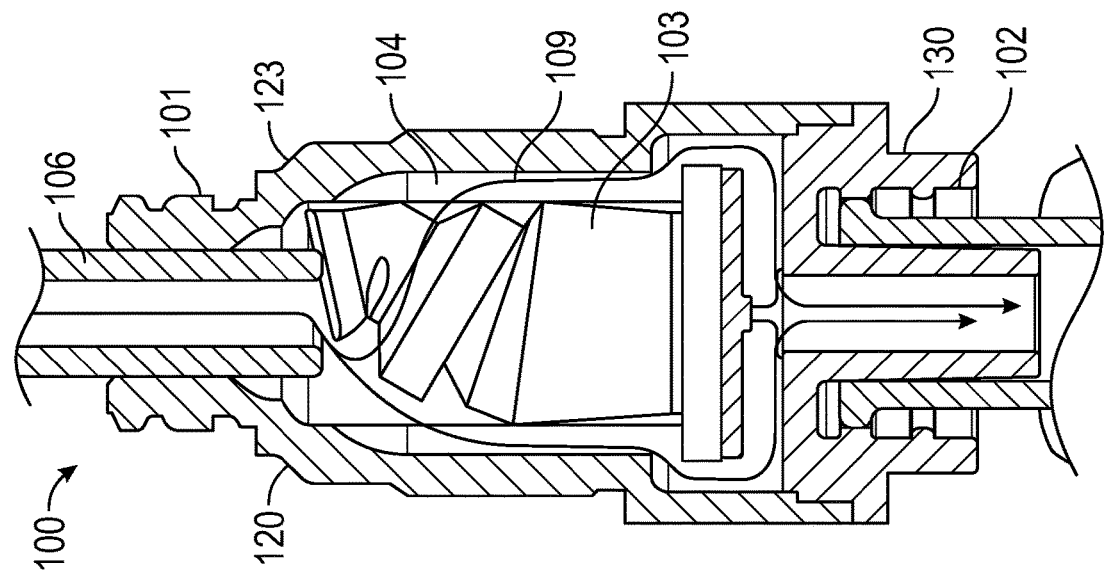
Figure 1C:
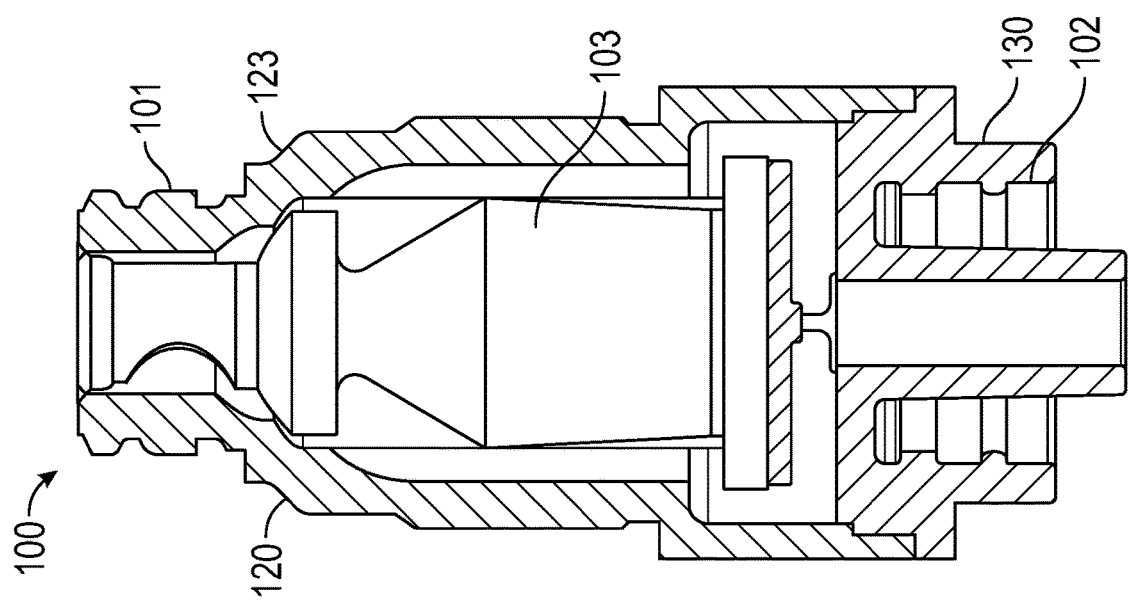

An example of an antimicrobial fluid transfer device implemented as a needleless access connector employing a valve is shown in FIGS. 1A-1C. FIG. 1A is a three-dimensional view showing components of a needless access connector 100 in unassembled form. FIGS. 1B and 1C are cut-away views of the assembled needless access connector 100 showing closed and open states, respectively.

Needleless access connector 100 includes housing 120, which has a female luer fitting 101 at its proximal end (on a top portion 123 of the housing) and a male luer fitting 102 at its distal end (on a base portion 130 of the housing). Although male and female luer fittings are shown, it will be appreciated that other types of connection interfaces may be employed without departing from principles described herein. Needless access connector 100 also includes a valve 103, which sits inside housing 120 and on top of base portion 130. Housing 120, including top portion 123 and base portion 130, can be made of rigid material, such as polycarbonate or another rigid plastic, and the valve 103 can be made from an elastic material, such as liquid silicone, so that it is collapsible within the housing 120. Additionally or alternatively, housing 120 and/or valve 103 may be made from, include, or otherwise be physically coupled to conductive materials that form electrodes capable of generating a galvanic electric field.

When in use, male luer fitting 102 is connected to, e.g., a catheter or to a female luer, and female luer fitting 101 is connected to a fluid reservoir, e.g., an IV bag or male luer. Female luer fitting 101 is connected to the fluid reservoir via a second male luer fitting 106, which has a hollow member (as shown in FIG. 1C) and is inserted through the top of female luer fitting 101. The insertion of male luer 106 collapses valve 103 down into internal cavity 104 to break the seal and open a fluid flow path 109. FIG. 1C shows collapsible valve 103 in the collapsed position after insertion of male luer 106 into female luer 101. Male luer 106 delivers fluid, e.g., from an IV bag, which flows through the internal cavity 104, around valve element 103, into channels in male luer fitting 102, and into the catheter or female luer.

Figure 2B:
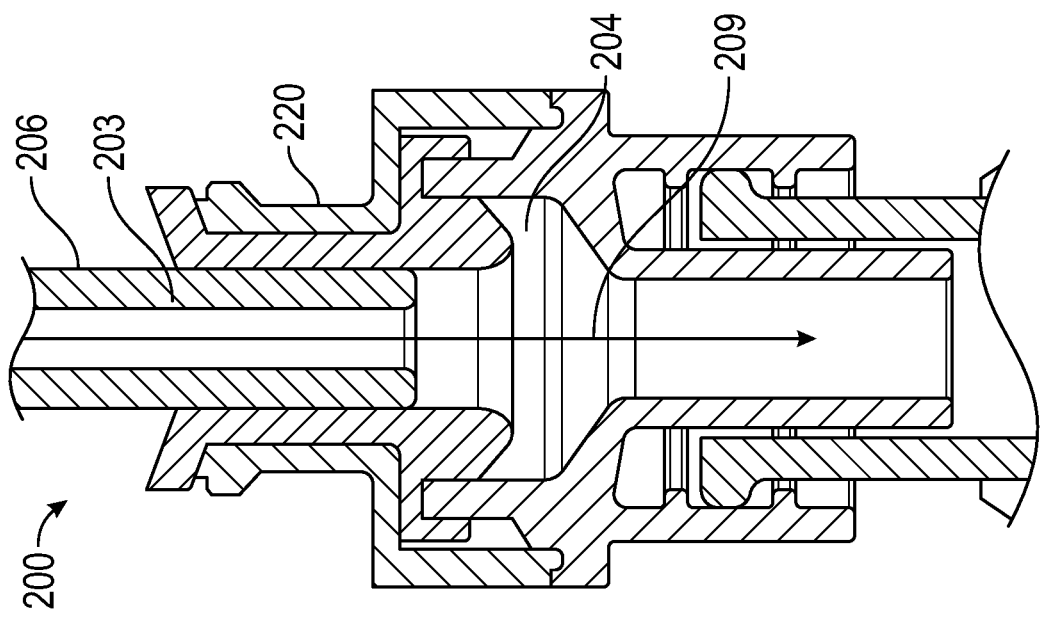
FIGS. 2A-2B are cut-away views of an example needless access connector showing closed and open states, respectively.
Figure 2A:
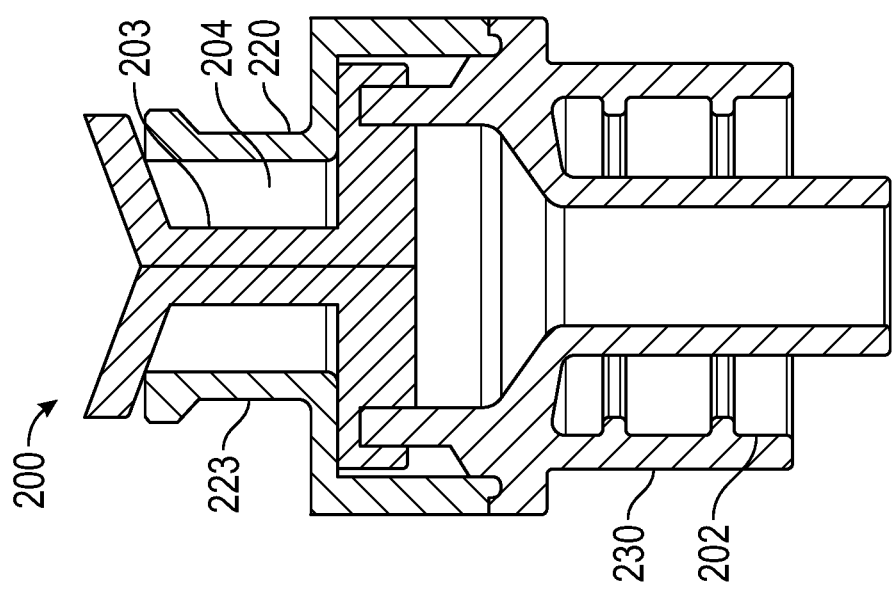

Another example of a needleless access connector employing a valve is shown in FIGS. 2A-2B. FIGS. 2A and 2B are cut-away views of the assembled needleless access connector 200 showing closed and open states, respectively.

The needleless access connector 200 is implemented as a split septum type of connector in which valve 203 is opened by piercing the proximal end of the connector with a blunt cannula 206. Needleless access connector 200 includes housing 220, which has a male luer fitting 202 at its distal end (on a base portion 230 of the housing). Needleless access connector 200 also includes a valve 203, which sits inside housing 220 and on top of base portion 230. Housing 220, including top portion 223 and base portion 230, can be made of rigid material, such as polycarbonate or another rigid plastic, and the valve 203 can be made from an elastic material, such as liquid silicone, so that it can separate within the housing 220 when opened and return to its original position to form a seal when closed. Additionally or alternatively, housing 220 and/or valve 203 may be made from, include, or otherwise be physically coupled to conductive materials that form electrodes capable of generating a galvanic electric field.

When in use, male luer fitting 202 is connected to, e.g., a catheter or to a female luer, and the proximal end is connected to a fluid reservoir, e.g., an IV bag or male luer. The insertion of blunt cannula 206 separates the valve 203 down into internal cavity 204 to break the seal and open a fluid flow path 209, which extends substantially straight through the housing 220 from the proximal end to the distal end. FIG. 2B shows split septum valve 203 in the separated and opened position after insertion of blunt cannula 206. Cannula 206 delivers fluid, e.g., from an IV bag, which flows through valve 203 and into the catheter or female luer.

The fluid passing through the fluid flow path 109 or fluid flow path 209 may be an electrolytic solution, such as saline, that forms a galvanic cell with electrodes coupled to the fluid flow path to activate an electric field. For example, with reference to FIGS. 1A-1C, dissimilar electrodes made from dissimilar conductive materials may be coupled to the valve 103 (e.g., disposed on an exterior surface thereof), coupled to the housing 120 (e.g., disposed on an interior surface thereof), or coupled to both the valve 103 and the housing 120 in a manner that permits contact with the fluid flow path 109. In some implementations, the housing 120 may be at least partially made from, include, or be otherwise coupled to one or more electrodes of a first type (e.g., Ag), and the valve 103 may be at least partially made from, include, or be otherwise coupled to one or more electrodes of a second type (e.g., Zn). An electrolytic solution (e.g., saline) flowing through the housing 120 or otherwise contacting the electrodes may activate an electric field to combat biofilm buildup. As another example, with reference to FIGS. 2A-2B, dissimilar electrodes made from dissimilar conductive materials may be coupled to the valve 203 (e.g., disposed on a surface between the split portion), coupled to the housing 220 (e.g., disposed on an interior surface thereof), or coupled to both the valve 203 and the housing 220 in a manner that permits contact with the fluid flow path 209.

Figure 3:
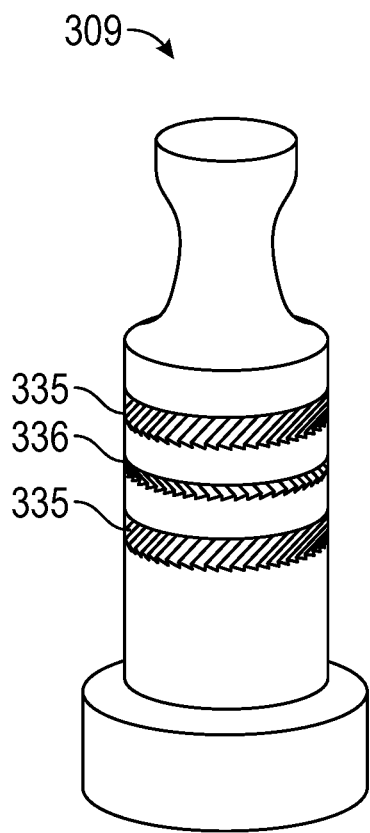
FIG. 3 is three-dimensional view of an example of a valve having an exemplary electrode arrangement.
Figure 4:
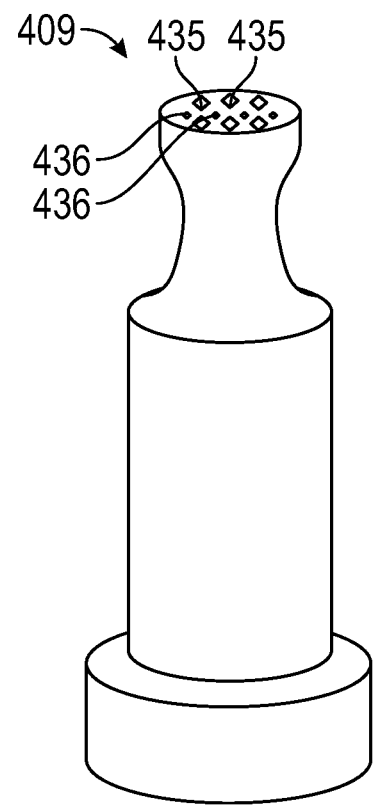
FIG. 4 is three-dimensional view of an example of a valve having an exemplary electrode arrangement.
Figure 5:
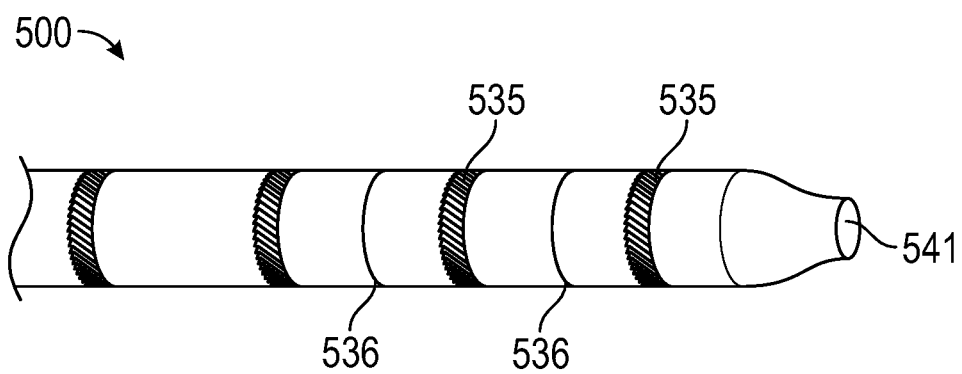
FIG. 5 is three-dimensional view of an example of a catheter having an exemplary electrode arrangement.

Examples of valves employing spaced apart electrodes are shown in FIGS. 3 and 4. An example of a catheter employing spaced apart electrodes is shown in FIG. 5. These examples illustrate some exemplary structural arrangements for galvanic electrodes in a fluid transfer device, but it will be appreciated that various other structural arrangements for electrodes in a needless connector, catheter, or other fluid transfer device are possible without departing from principles described herein.

FIG. 3 is a three-dimensional view of a valve 309, which may be included in a needless connector within an interior cavity of a connector housing. The valve 309 includes a plurality of annular electrodes 335, 336, which are disposed around the valve on an exterior surface thereof. The electrodes include a plurality of electrodes 335 of a first type of conductive material (e.g., Ag) and an electrode 336 of a second type of material (e.g., Zn) interposed between the electrodes 335. The electrode 335 is also shown with a thinner structure than the electrodes 336. Although only three electrodes are shown, more electrodes may be included. For example, four, five, six, eight, ten, twenty, fifty, or more electrodes may be configured with a repeating or alternating pattern (e.g., cathode, anode, cathode, anode, and so forth). Although the electrodes 335, 336 are shown positioned on a surface of the valve 309, it is possible for either one or both types of annular electrodes 335, 336 to be disposed around the valve 309 by positioning them on an interior surface of the housing, for example. Each electrode may be disposed on a non-conductive surface and generally spaced apart from the other electrodes to avoid ohmic contact with each other when in an inactive state.

FIG. 4 is a three-dimensional view of a valve 409 that may be included in a needless connector within an interior cavity of a connector housing. The valve 409 includes a plurality of electrodes islands 435, 436 (or "dots") disposed on a proximal tip of the valve 409 corresponding to a fluid entry end of the needless connector. Multiple electrode islands 435 of a first type of conductive material (e.g., Ag) are arranged in a two dimensional matrix interposed with multiple electrode islands 436 of a second type of conductive material (e.g., Zn). The multiple electrode islands 436 of the second type are also each shown as being generally smaller than the first type of electrode islands 435. Employing multiple electrodes of one or both types of electrode in a matrix or repeating pattern, such as the examples shown in FIG. 3 or 4, allows for the creation of multiple galvanic cells in accordance with multiple pairings of dissimilar electrodes.

An example of a catheter employing galvanic electrodes is depicted in FIG. 5. FIG. 5 is a three-dimensional view of a catheter 500 designed to be inserted into a cavity of a patient's body and left in the patient for an extended period of time. The catheter 500 includes a tubular member having a lumen 541 extending therethrough to provide a fluidic pathway for transferring fluid between a patient and a fluid reservoir to or from the patient. The catheter 500 further includes annular electrodes 535 having a first conductive material and annular electrodes 536 having a second conductive material different from the first conductive material and interposed between the first electrodes 535 in an alternating pattern. The second type of electrodes 536 are also shown as thinner and smaller than the first type of electrodes 535. The components of the catheter 500 shown in FIG. 5 may be configured to remain in a patient for a prolonged period of time, and the electrodes 535, 536 may activate a galvanic electric field or current in response to contact with body fluid or tissue of the patient.

According to some embodiments, an indicator may be provided on a fluid transfer device to provide a mechanism for indicating a charge remaining in a galvanic cell. This may be useful to, for example, indicate a lifetime remaining for antimicrobial functions of the device and inform a decision of a medical practitioner (e.g., a nurse or a doctor) to change or replace the device.

Figure 6:
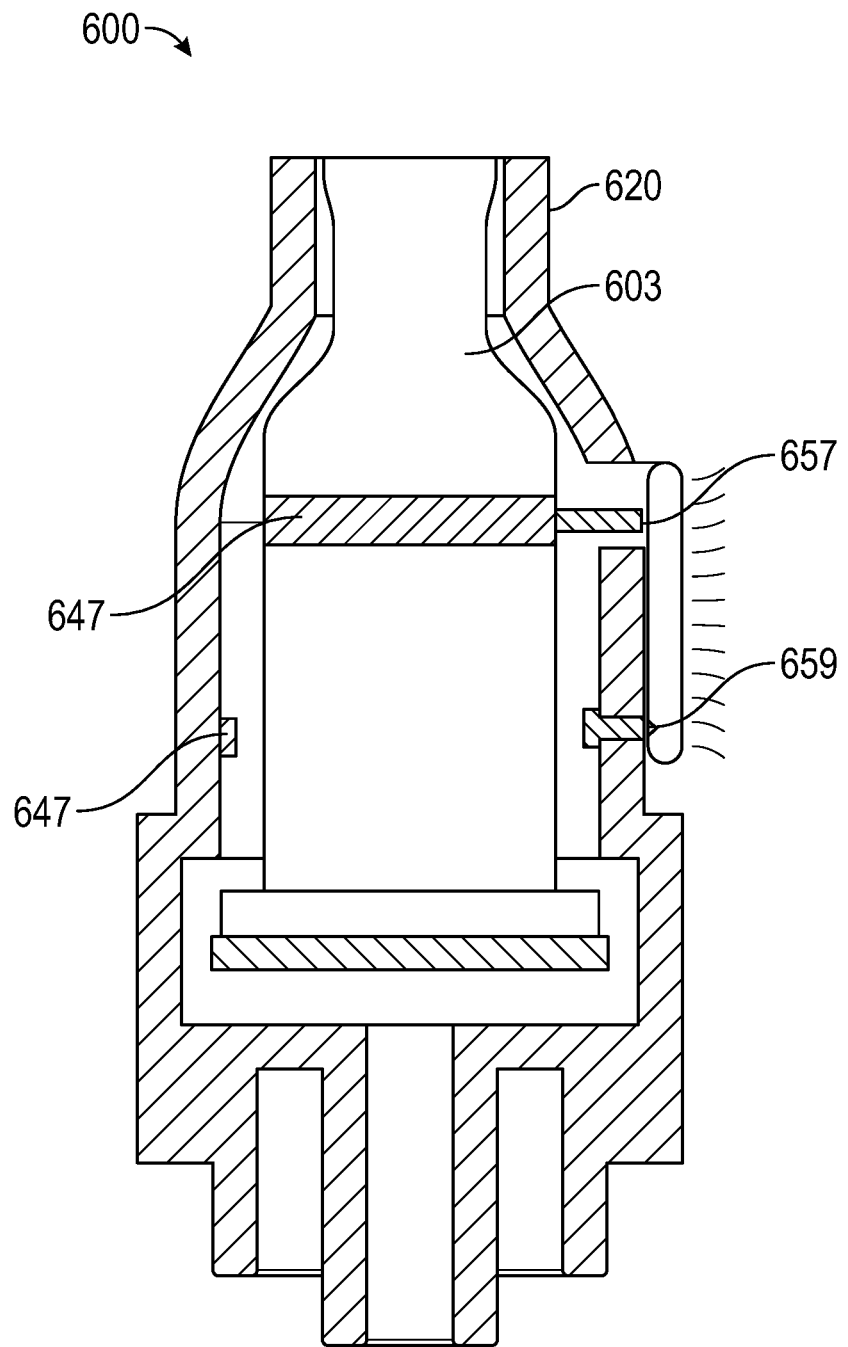
FIG. 6 is a cut-away schematic view of an example of a fluid transfer device having an exemplary indicator.

An example of an indicator coupled to a needless connector is shown in FIG. 6. FIG. 6 is a cut-away view of needless access connector 600 including a housing 620 and a valve 603 disposed within an interior cavity of the housing 620. The needless access connector 600 may, for example, share features in common with any of the above described needless access connectors. Additionally or alternatively, the needless access connector 600 can include an indicator 652 operatively coupled to electrodes 647 disposed on the housing 620 and/or valve 603. The indicator 652 includes a first contact 657 operatively coupled to at least one electrode of a first type, and a second contact 659 operatively coupled to at least one electrode of a second type. A thermochromic material (e.g., ink or dye) is coupled between the first contact 657 and second contact 659 and visible from an exterior of the housing 620.

A compressible insulating material and/or space may separate the first contact 657 from the first electrode(s) and the second contact 659 from the second electrode(s) when in a neutral or uncompressed state. When a user (e.g., a medical practitioner) presses against the first contact 657 and the second contact 659, this causes the first contact 657 and the second contact 659 to contact the first and second electrodes, respectively, and complete a circuit that causes current to through the thermochromic material. The thermochromic material is temperature sensitive and provides a varying visual appearance (e.g., changed color) in relation to its temperature. A resistance in or coupled to the thermochromic material may also cause increased heat generation or temperature in relation to increased current. As a result, the appearance of the thermochromic material provides a visual indication of the amount of current flowing through it, and thus, the amount of charge remaining in the galvanic cell(s). Additionally or alternatively, other components that produce a perceptible visual change in response to changes in current, voltage, and/or heat can be used in the indicator circuit, such as thermoluminescent and/or electroluminescent materials.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. An antimicrobial medical device comprising: a fluid transfer device configured to couple between a patient and a fluid reservoir; a fluid pathway extending through the fluid transfer device; at least one first electrode coupled to the fluid transfer device, the at least one first electrode comprising a first conductive material; and at least one second electrode coupled to the fluid transfer device and spaced apart from the at least one first electrode, the at least one second electrode comprising a second conductive material different from the first conductive material and being configured to form at least one galvanic cell with the at least one first electrode.

Clause 2. The medical device of Clause 1, wherein the fluid transfer device comprises a housing having an internal cavity, and a valve disposed within the internal cavity, wherein the fluid pathway extends through the housing, and wherein the at least one first electrode and the at least one second electrode are coupled to the fluid pathway.

Clause 3. The medical device of Clause 2, wherein the at least one first electrode is coupled to the housing and the at least one second electrode is coupled to the valve.

Clause 4. The medical device of Clause 3, wherein the housing is made from a rigid non-conductive material, the first conductive material is disposed on a surface of the rigid non-conductive material, the valve is made from an elastic non-conductive material, and the second conductive material is disposed on a surface of the elastic non-conductive material.

Clause 5. The medical device of Clause 3, wherein the housing is at least partially made from the first conductive material, and wherein the valve is at least partially made from the second conductive material.

Clause 6. The medical device of Clause 2, wherein the at least one first electrode and the at least one second electrode are coupled to the valve.

Clause 7. The medical device of Clause 2, wherein the at least one first electrode and the at least one second electrode are coupled to the housing.

Clause 8. The medical device of Clause 2, wherein at least one first electrode comprises a plurality of first annular electrodes disposed around the valve, and wherein the at least one second electrode comprises a second annular electrode interposed between the plurality of first annular electrodes.

Clause 9. The medical device of Clause 2, wherein the at least one first electrode comprises a plurality of first electrode islands disposed on the valve and the at least one second electrode comprises a plurality of second electrode islands disposed on the valve and interposed between the plurality of first electrode islands.

Clause 10. The medical device of Clause 9, wherein the plurality of first electrode islands and the plurality of second electrode islands are disposed on a proximal tip of the valve, the proximal tip corresponding to a fluid entry end of the valve.

Clause 11. The medical device of any preceding Clause wherein the fluid transfer device comprises a lumen providing the fluid pathway, and wherein the at least one first electrode and the at least one second electrode are disposed around the fluid pathway.

Clause 12. The medical device of Clause 11, wherein the at least one first electrode comprises a plurality of first annular electrodes, and the at least one second electrode comprises a plurality of second annular electrodes interposed between the plurality of first annular electrodes.

Clause 13. The medical device of Clause 12, wherein the plurality of second annular electrodes are thinner than the plurality of first annular electrodes.

Clause 14. The medical device of any preceding Clause, wherein the first conductive material comprises one of silver or zinc, and the second conductive material comprises the other of silver or zinc.

Clause 15. The medical device of any preceding Clause, further comprising: an indicator comprising (i) a first contact configured to connect to the at least one first electrode, (ii) a second contact configured to connect to the at least one second electrode, and (iii) at least one of a thermochromic, thermoluminescent, or electroluminescent material visible from an exterior of the fluid transfer device and coupled between the first contact and the second contact.

Clause 16. An antimicrobial needless connector comprising: a housing having an internal cavity and configured to couple between a patient and a fluid reservoir; a fluid pathway extending through the housing; a valve disposed within the internal cavity and configured to open and close the fluid pathway; at least one first electrode coupled the housing, the valve, or a combination thereof, the at least one first electrode comprising a first conductive material; and at least one second electrode coupled to the housing, the valve, or a combination thereof, the at least one second electrode being spaced apart from the at least one first electrode, the at least one second electrode comprising a second conductive material different from the first conductive material and being configured to form at least one galvanic cell with the at least one first electrode.

Clause 17. The needless connector of Clause 16, wherein the at least one first electrode is coupled to the housing and the at least one second electrode is coupled to the valve.

Clause 18. The needless connector of Clause 17, wherein the housing is made from a rigid non-conductive material, the first conductive material is disposed on a surface of the rigid non-conductive material, the valve is made from an elastic non-conductive material, and the second conductive material is disposed on a surface of the elastic non-conductive material.

Clause 19. The needless connector of Clause 17, wherein the housing is at least partially made from the first conductive material, and wherein the valve is at least partially made from the second conductive material.

Clause 20. The needless connector of Clause 16-19, wherein the at least one first electrode and the at least one second electrode are coupled to the valve.

Clause 21. The needless connector of Clause 16-20, wherein the at least one first electrode and the at least one second electrode are coupled to the housing.

Clause 22. The needless connector of Clause 16-21, wherein the at least one first electrode comprises a plurality of first annular electrodes disposed around the valve, and wherein the at least one second electrode comprises a second annular electrode interposed between the plurality of first annular electrodes.

Clause 23. The needless connector of Clause 16-22, wherein the at least one first electrode comprises a plurality of first electrode islands disposed on the valve and the at least one second electrode comprises a plurality of second electrode islands disposed on the valve and interposed between the plurality of first electrode islands.

Clause 24. The needless connector of Clause 23, wherein the plurality of first electrode islands and the plurality of second electrode islands are disposed on a proximal tip of the valve, the proximal tip corresponding to a fluid entry end of the valve.

Clause 25. The needless connector of Clause 16-24, wherein the first conductive material comprises one of silver or zinc, and the second conductive material comprises the other of silver or zinc.

Clause 26. An antimicrobial catheter comprising: a tubular member configured to couple between a patient and a fluid reservoir; a lumen extending through the tubular member and providing a fluid pathway to transfer fluid; at least one first electrode disposed around the fluid pathway, the at least one first electrode comprising a first conductive material; and at least one second electrode disposed around the fluid pathway and spaced apart from the at least one first electrode, the at least one second electrode comprising a second conductive material different from the first conductive material and being configured to form at least one galvanic cell with the at least one first electrode.

Clause 27. The catheter of Clause 26, wherein the at least one first electrode comprises a plurality of first annular electrodes, and the at least one second electrode comprises a plurality of second annular electrodes interposed between the plurality of first annular electrodes.

Clause 28. The catheter of Clause 27, wherein the plurality of second annular electrodes are thinner than the plurality of first annular electrodes.

Clause 29. The catheter of Clause 26-28, wherein the first conductive material comprises one of silver or zinc, and the second conductive material comprises the other of silver or zinc.

Clause 30. A fluid transfer device according to any of Clauses 1-15.

Clause 31. A needless access connector according to any of Clauses 1-15.

Clause 32. A catheter according to any of Clauses 1-15.

A reference to an element in the singular is not intended to mean one and only one unless specifically so stated, but rather one or more. For example, "a" module may refer to one or more modules. An element proceeded by "a," "an,"

"the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) or § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. An antimicrobial needleless connector comprising:
    a housing having an internal cavity and configured to couple between a patient and a fluid reservoir;
    a fluid pathway extending through the housing;
    a valve disposed within the internal cavity and configured to open and close the fluid pathway;
    a plurality of first annular electrodes coupled the housing, the valve, or a combination thereof, wherein the plurality of first annular electrodes are disposed around the valve, the plurality of first annular electrodes comprising a first conductive material; and
    at least one second annular electrode coupled to the housing, the valve, or a combination thereof, the at least one second annular electrode being spaced apart and interposed between the plurality of first annular electrodes, the at least one second annular electrode comprising a second conductive material different from the first conductive material and being configured to form at least one galvanic cell with the at least one first electrode.

2. The needleless connector of claim 1, wherein the plurality of first annular electrodes is coupled to the housing and the at least one second annular electrode is coupled to the valve.

3. The needleless connector of claim 2, wherein the housing is made from a rigid non-conductive material, the first conductive material is disposed on a surface of the rigid non-conductive material, the valve is made from an elastic non-conductive material, and the second conductive material is disposed on a surface of the elastic non-conductive material.

4. The needleless connector of claim 2, wherein the housing is at least partially made from the first conductive material, and wherein the valve is at least partially made from the second conductive material.

5. The needleless connector of claim 1, wherein the plurality of first annular electrodes and the at least one second annular electrode are coupled to the valve.

6. The needleless connector of claim 1, wherein the plurality of first annular electrodes and the at least one second annular electrode are coupled to the housing.

7. The needleless connector of claim 1, wherein the first conductive material comprises one of silver or zinc, and the second conductive material comprises the other of silver or zinc.

8. An antimicrobial needleless connector comprising:
a housing having an internal cavity and configured to couple between a patient and a fluid reservoir;
a fluid pathway extending through the housing;
a valve disposed within the internal cavity and configured to open and close the fluid pathway;
a plurality of first electrode islands coupled the housing, the valve, or a combination thereof, wherein the plurality of first electrode islands are disposed on the valve, the plurality of first electrode islands comprising a first conductive material; and
a plurality of second electrode islands coupled to the housing, the valve, or a combination thereof, wherein the plurality of second electrode islands are disposed on the valve, the plurality of second electrode islands being spaced apart and interposed between the plurality of first electrode islands, the plurality of second electrode islands comprising a second conductive material different from the first conductive material, being configured to form at least one galvanic cell with the plurality of first electrode islands, wherein the plurality of first electrode islands and the plurality of second electrode islands are disposed on a proximal tip of the valve, the proximal tip corresponding to a fluid entry end of the valve.

9. The needleless connector of claim 8, wherein the plurality of first electrode islands is coupled to the housing and the plurality of second electrode islands is coupled to the valve.

10. The needleless connector of claim 9, wherein the housing is made from a rigid non-conductive material, the first conductive material is disposed on a surface of the rigid non-conductive material, the valve is made from an elastic non-conductive material, and the second conductive material is disposed on a surface of the elastic non-conductive material.

11. The needleless connector of claim 9, wherein the housing is at least partially made from the first conductive material, and wherein the valve is at least partially made from the second conductive material.

12. The needleless connector of claim 8, wherein the plurality of first electrode islands and the plurality of second electrode islands are coupled to the valve.

13. The needleless connector of claim 8, wherein the plurality of first electrode islands and the plurality of second electrode islands are coupled to the housing.

14. The needleless connector of claim 8, wherein the first conductive material comprises one of silver or zinc, and the second conductive material comprises the other of silver or zinc.

* * * * *